(12) United States Patent
Madeira

(10) Patent No.: US 11,406,816 B2
(45) Date of Patent: Aug. 9, 2022

(54) SYSTEM AND METHODS FOR PERCUTANEOUS MECHANICAL AND/OR NEURAL INTERFACE

(71) Applicant: Robert Madeira, Allentown, PA (US)

(72) Inventor: Robert Madeira, Allentown, PA (US)

( * ) Notice: Subject to any disclaimer, the term of this patent is extended or adjusted under 35 U.S.C. 154(b) by 155 days.

(21) Appl. No.: 16/852,576

(22) Filed: Apr. 20, 2020

(65) Prior Publication Data

US 2020/0238077 A1 Jul. 30, 2020

Related U.S. Application Data

(62) Division of application No. 15/707,185, filed on Sep. 18, 2017, now Pat. No. 10,675,456.

(Continued)

(51) Int. Cl.
*A61F 2/78* (2006.01)
*A61N 1/05* (2006.01)
(Continued)

(52) U.S. Cl.
CPC .............. *A61N 1/0551* (2013.01); *A61B 5/24* (2021.01); *A61B 5/685* (2013.01); *A61B 5/6877* (2013.01); *A61B 5/6884* (2013.01); *A61F 2/0063* (2013.01); *A61F 2/02* (2013.01); *A61F 2/0811* (2013.01); *A61F 2/2814* (2013.01); *A61F 2/30907* (2013.01); *A61F 2/389* (2013.01); *A61F 2/3859* (2013.01); *A61F 2/60* (2013.01); *A61F 2/78* (2013.01); *A61N 1/18* (2013.01); *A61N 1/36003* (2013.01); *A61F 2002/0068* (2013.01); *A61F 2002/087* (2013.01); *A61F 2002/0823* (2013.01); *A61F 2002/0852* (2013.01); *A61F 2002/2825* (2013.01); *A61F 2002/30602* (2013.01); *A61F 2002/30607* (2013.01); *A61F 2002/30884* (2013.01); *A61F 2002/3881* (2013.01);
(Continued)

(58) Field of Classification Search
CPC .... A61N 1/0551; A61N 1/18; A61N 1/36003; A61B 5/24; A61B 5/685; A61B 5/6877; A61B 5/6884; A61F 2/0063; A61F 2/02; A61F 2/0811; A61F 2/30907; A61F 2/3859; A61F 2/389; A61F 2/60; A61F 2/72; A61F 2/78; A61F 2/2814
See application file for complete search history.

(56) References Cited

U.S. PATENT DOCUMENTS 7,018,420 B2 * 3/2006 Grundei ................ A61F 2/2814
623/32
7,083,648 B2 * 8/2006 Yu ............................ A61F 2/60
604/174
(Continued)

*Primary Examiner* — Bruce E Snow

(57) ABSTRACT

A system and method for improving limb function through the use of percutaneous mechanical and neural interfaces. The system generally uses a hollow long bone axial rod that is inserted into the long bone medullary cavity. A transfer rod with a central channel is mounted to the long bone axial rod. An exterior body attachment is connected to the transfer rod and attachment rings attach muscle groups, fascia layers and dermal layers to the transfer rod. Additionally, the system is configured to collect and transmit nerve signaling data to an external processor and additionally configured to transmit data from the external processor to the plurality of nerves.

10 Claims, 10 Drawing Sheets

Related U.S. Application Data

(60) Provisional application No. 62/495,625, filed on Sep. 20, 2016.

(51) Int. Cl.
    *A61N 1/36*     (2006.01)
    *A61N 1/18*     (2006.01)
    *A61F 2/38*     (2006.01)
    *A61F 2/60*     (2006.01)
    *A61F 2/08*     (2006.01)
    *A61F 2/30*     (2006.01)
    *A61F 2/00*     (2006.01)
    *A61F 2/02*     (2006.01)
    *A61B 5/00*     (2006.01)
    *A61B 5/24*     (2021.01)
    *A61F 2/28*     (2006.01)

(52) U.S. Cl.
    CPC ... *A61F 2002/607* (2013.01); *A61F 2002/608* (2013.01); *A61F 2002/7881* (2013.01); *A61F 2002/7887* (2013.01); *A61N 1/0558* (2013.01); *A61N 1/36057* (2013.01)

(56) References Cited

U.S. PATENT DOCUMENTS

| | | |
|---|---|---|
| 7,137,998 B2 | 11/2006 | Bedard |
| 7,302,296 B1 | 11/2007 | Hoffer |
| 8,057,550 B2 | 11/2011 | Clausen |
| 8,323,354 B2 | 12/2012 | Bedard |
| 8,512,416 B2 | 8/2013 | Porter |
| 8,591,599 B1 | 11/2013 | Kaliki |
| 8,598,815 B2 | 12/2013 | Glaister |
| 8,628,585 B2 | 1/2014 | Harris |
| 8,814,949 B2 | 8/2014 | Gramnaes |
| 9,044,347 B2 | 6/2015 | Cederna |
| 9,067,057 B2 * | 6/2015 | Branemark .......... A61F 2/2814 |
| 9,155,634 B2 | 10/2015 | Lipschutz |
| 9,339,396 B2 | 5/2016 | Wilkinson |
| 9,358,137 B2 | 6/2016 | Bedard |
| 9,555,235 B2 | 1/2017 | Achyuta |
| 9,579,222 B2 | 2/2017 | Branemark |
| 2004/0172138 A1 * | 9/2004 | May ..................... A61F 2/3607 623/23.26 |
| 2006/0095140 A1 * | 5/2006 | Steinbarger ............ A61F 2/76 623/38 |
| 2014/0277583 A1 | 9/2014 | Kuntaegowdanahalli |
| 2015/0265430 A1 * | 9/2015 | Branemark ............ A61F 2/76 623/32 |
| 2016/0058519 A1 | 3/2016 | Herr |
| 2016/0151174 A1 * | 6/2016 | Radzinsky ............. A61F 2/76 623/38 |
| 2016/0180054 A1 | 6/2016 | Luo |
| 2016/0207201 A1 | 7/2016 | Herr |
| 2016/0287422 A1 | 10/2016 | Kelly |
| 2016/0331561 A1 | 11/2016 | Raspopovic |
| 2016/0346099 A1 | 12/2016 | Herr |
| 2017/0020693 A1 | 1/2017 | Harshbarger |
| 2019/0053920 A1 * | 2/2019 | Armitage ................. A61F 2/80 |
| 2021/0137563 A1 * | 5/2021 | Forsberg ............... A61B 17/74 |

* cited by examiner

SYSTEM AND METHODS FOR PERCUTANEOUS MECHANICAL AND/OR NEURAL INTERFACE

RELATED APPLICATIONS

This application claims priority to U.S. Provisional Application No. 62/495,625 filed Sep. 20, 2016. Further, this application claims priority to U.S. patent application Ser. No. 15/707,185 filed Sep. 18, 2017. The entire contents of the above applications are hereby incorporated by reference as though fully set forth herein.

FIELD

The present invention relates to the field of human-machine interfaces. More specifically, the present invention relates to mechanical-neuro connection systems for attachment of objects to the body.

BACKGROUND

Amputation is the removal of a limb by trauma, medical illness, or surgery. A prosthetic is an artificial device that replaces an amputated or otherwise missing body part, which may be amputated or lost through trauma, disease, or congenital conditions. There are several ways a prosthesis can be attached to a stump. It may be held on with suction, a locking pin, or with a harness. Each method has advantages and drawbacks. A harness can be bulky and not move as well as the other systems. A locking pin may cause irritation where it contacts the stump. Suction is generally considered the best choice, but the user must put the prosthesis on accurately in order to get secure suction.

These methods are not conducive to use of a variety of exterior attachments other than prosthetic devices, such as a tool, for example. Nor are they able to capture and utilize nervous system signaling in any meaningful fashion. Thus, it would be useful to have a new system and method to improve limb function after amputation that also allows a significantly higher degree of human-machine interface.

BRIEF SUMMARY OF THE INVENTION

It is the object of the present invention to provide a new system and method for improving limb function through the use of mechanical and percutaneous neural interfaces. One embodiment of the present invention is system for attachment of a device to a bone. It is comprised generally of a hollow long bone axial rod inserted into the long bone medullary cavity; a transfer rod with a central channel mounted to the long bone axial rod; an exterior body attachment connected to the transfer rod at the end opposite the long bone axial rod; and attachment rings for attaching muscle groups, fascia layers and dermal layers to the transfer rod. Additionally, this embodiment of the present invention may include a system configured to collect and transmit nerve signaling data to an external processor and additionally configured to transmit data from the external processor to the nerves.

In a second embodiment of the present invention, a system for attachment of a device in a transverse direction to a bone is disclosed. It is comprised generally of a central bone implant; a subcutaneous central mount with a central channel that can be viewed from the top of the skin that is inserted and secured into the central bone implant; a stud connector locked into the central mount; and a spring for pressure loading the central mount in a locked position.

A third embodiment of the present invention is a system for attachment of a device to a bone. It is comprised generally of a device with female socket connectors at one end; a hollow long bone axial rod that inserts into a long bone medullary cavity; and a transfer rod mounted to long bone axial rod with at matching male ratchet connectors separated by a central rod portion. The male ratchet connectors are inserted into the female socket connectors using a ratchet retention spring ball system.

DETAILED DESCRIPTION

Figure 1:
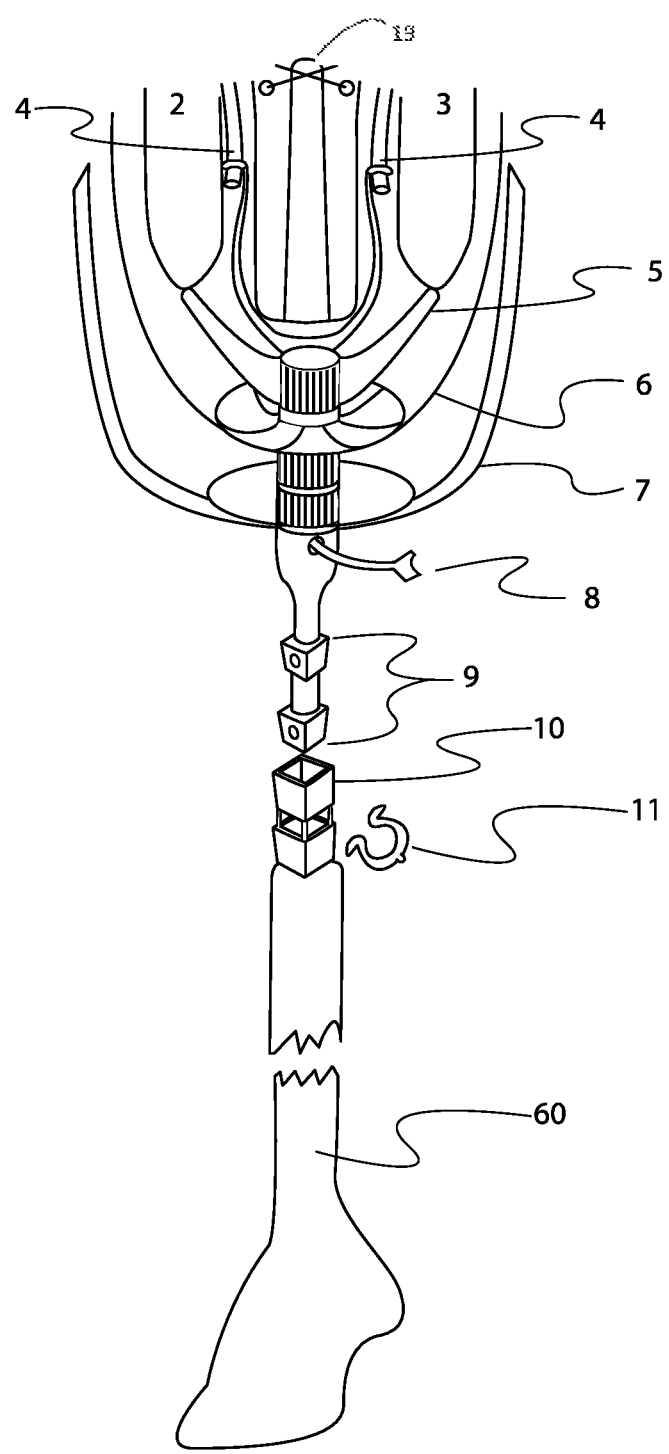
FIG. 1 is front view of an embodiment of the present invention.

Turning to FIG. 1, a summary view of an embodiment of the present invention is shown with the following general components: a first muscle group 2, second muscle group 3, nerve attachment clips 4, muscular attachment ring 5, fascia attachment ring 6, dermal/epidermal attachment ring 7, nerve signal processor attachment connector 8, prosthetic rod attachment ratchet (male) 9, prosthetic device attachment socket (female) 10, prosthetic attachment retention clip 11. Part 60 represents any compatible prosthetic attachment.

Figure 2:
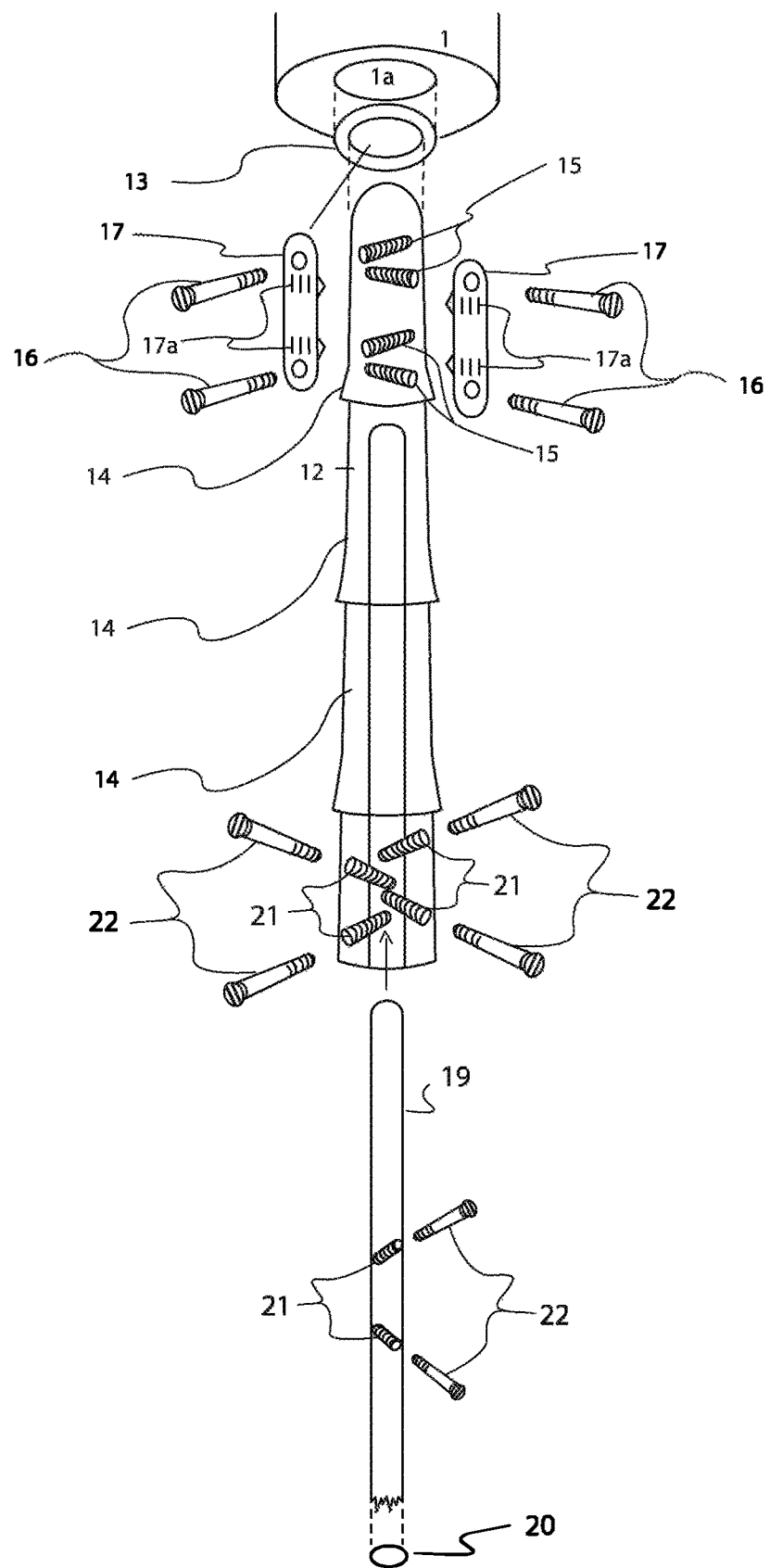
FIG. 2 is an exploded view of a portion of an embodiment of the invention of FIG. 1.

Turning to FIG. 2, most of the attachment to the axial skeleton long bone is by lengthwise long bone axial rods composed of nickel-titanium or equivalent bio-acceptable material. An embodiment includes a distal end amputation long bone 1 with prosthetic rod inserted into the long bone medullary cavity 1a. The long bone rod 12 inserts into the long bone medullary cavity 1a. The rods are substantially oblong in cross section. The oblong cross section transfers rotational forces to the long bone and keeps the implant from rotating within the long bone medullary cavity. The long bone rod is hollow for accepting the transfer rod 19.

The long bone rod has wedge-like flare-anchors 14 along the long-bone implant. The implant flare-anchors 14 support the implant against extrinsic forces that will pull at the implant, such as carrying a weight in a prosthetic forearm. Additionally, the long-bone implant has mounting bores 15 through which screws 16 attach fixation plates 17 which are external to the bone, and provide additional mounting stability against forces transmitting from the external environment to long bone of the body. The diagram shows multiple bore holes and screws, but not all will necessary be utilized at the time of implantation.

The fixation plates 17 have several rows of mounting teeth 17a to grip into the cortical bone as a structural interface. The long bone implant rod 12 is hollow and accepts an inserted internal to external (I/O) transfer rod 19. The I/O rod 19 (see FIGS. 1 and 3) is the physical connection between the long bone implant and the soft tissues of the limb. It interfaces to the soft tissues of the limb by various PEEK rings. It connects to external prosthetics by a male/female dual ratchet—socket mechanism shown as 9 and 10, respectively. The I/O rod 19 is also a substantially oblong ellipse 20 for transfer of rotation forces.

The I/O rod 19 is mounted to the distal end of the long-bone rod 12 by screw bores 21 and fixation screws 22. The diagram shows multiple bore holes and screws, but not all will necessary be utilized at the time of implantation.

Figure 3:
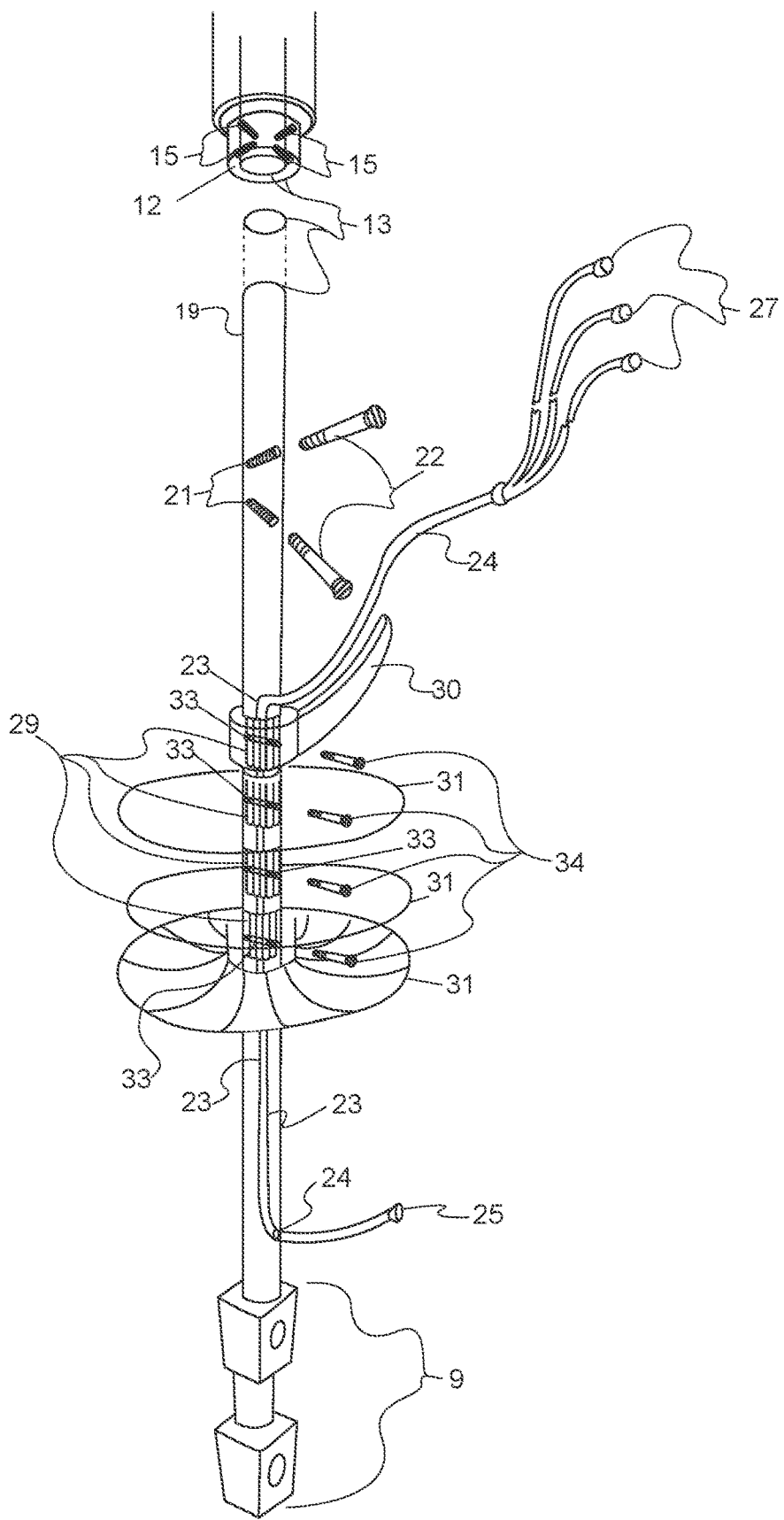
FIG. 3 is an exploded view of a portion of an embodiment of the invention of FIG. 1.

Turning to FIG. 3, "PEEK" stands for polyetheretherketone, which is a semi-crystalline, high temperature plastic. It is chosen to represent any selection of a large family of bio-neutral polymers available for surgical implantation purposes.

The long bone axial rod 12 has bore holes 15, as does the I/O transfer rod 19, through which fixation screws 22 mount. The I/O transfer rod 19 is also substantially oblong in cross section 13, to transmit rotational force along the axis of the rod-to-long-bone-implant interface.

The transfer rod 19 has a central channel 23, through which a sealed micro-wire cable 24 insulated with PEEK or other bio-acceptable dielectric material, attaches to a modified Utah Array 46, which itself interfaces to a nerve/nerve bundle. The micro wire 24 runs from inside the limb or body region nerve attachment site, then passes down through the I/O rod 19, and exits the I/O rod to the exterior of the body, where it can attach by an appropriate connector to an external processor 25.

The micro-wire cables 24 can come in bundles 27, and attach to micro connectors that clamp directly onto an associated nerve or nerve bundle (see FIG. 4). The transfer rod 19 has multiple sequential areas of gear-like ridges 29 about 1-2 cm wide, to which mating slotted rings 30 and 31 will allow full attachment to the rod for various connective purposes and at various tissue layers.

Referring to FIGS. 3, 4A-4C, and 5A-5D, in general, there is an attachment ring for any PEEK-ring to limb tissue layer attachments. Attachment rings may be for one, two, three, four or more associated muscle groups 31. There are PEEK-ring attachments for tissue closure at the fascia and dermal layers 32. Each PEEK-ring will attach by sliding into position. All PEEK rings are bore hole 33 and screw 34 mounted, or have clamped rings 36 that are bore hole/screw mounted, and closure clip retained.

At the end of the transfer rod 19, external to the limb or other bodily attachment point, is a dual ratchet type connector 9 sized for appropriate load bearing, with each ratchet dimension likely ranging from about 1 to about 2.5 cm range on each side.

There is a simple ratchet retention spring-ball system for initial connection, and between the two ratchet areas is a central rod area for a retention clip 11 to maintain definitive attachment of external prosthetic devices.

Figure 4A:
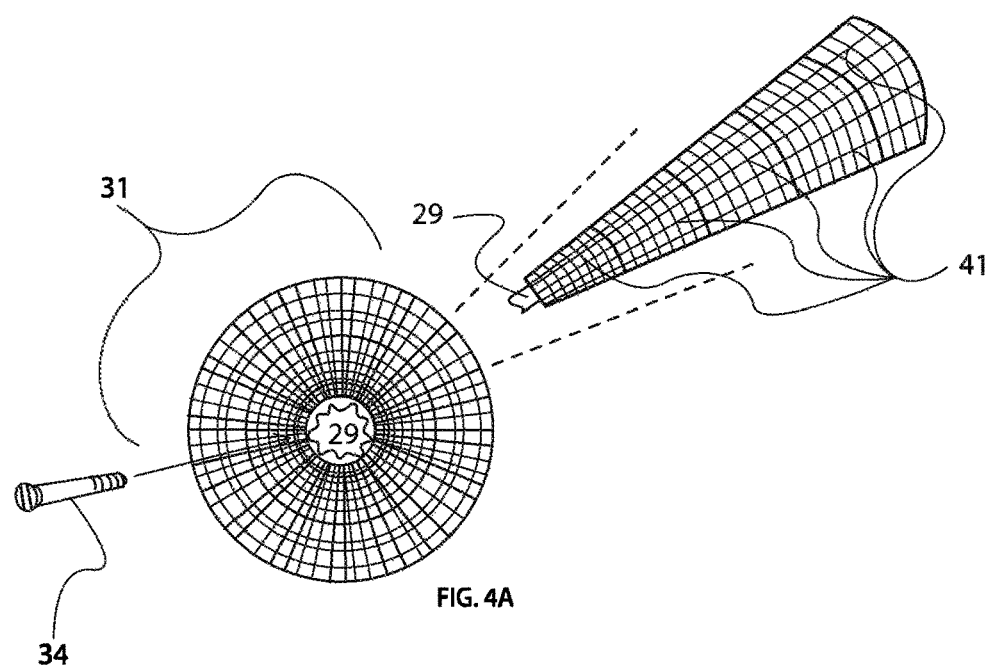
FIG. 4A is an exploded view of the attachment rings of an embodiment of the present invention.
Figure 4B:
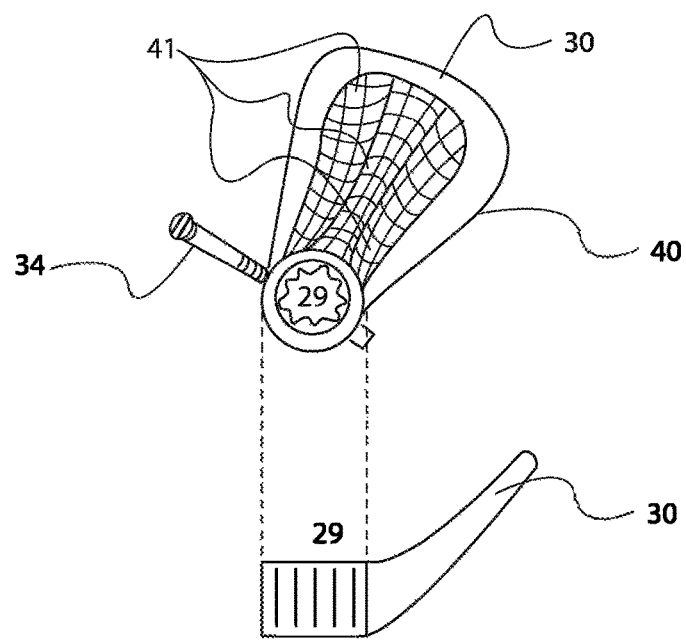
FIG. 4B is an exploded view of attachment rings of an embodiment of the present invention.
Figure 4C:
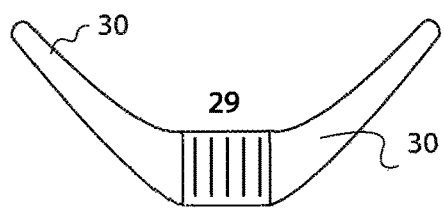
FIG. 4C is an alternative embodiment of the attachment rings of an embodiment of the present invention.
Figure 5A:
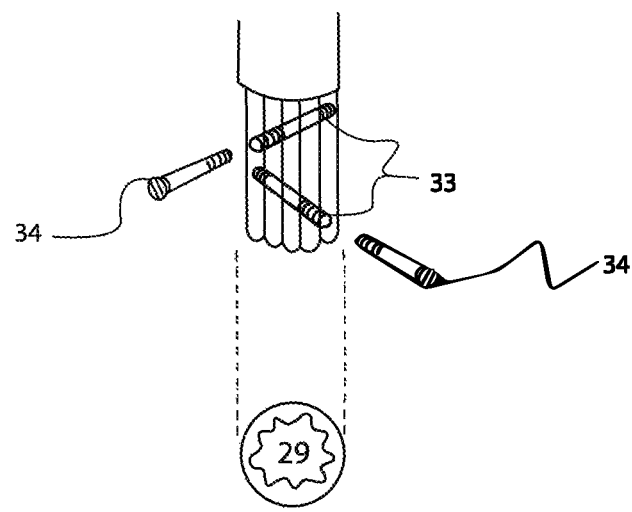
FIG. 5A is an expanded view of a portion of the attachment rings of an embodiment of the present invention.
Figure 5B:
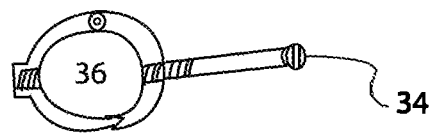
FIG. 5B is an expanded view of a portion of the attachment rings of an embodiment of the present invention.
Figure 5C:
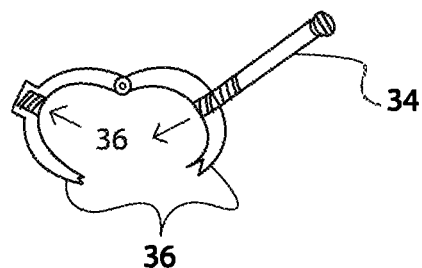
FIG. 5C is an expanded view of a portion of the attachment rings of an embodiment of the present invention.
Figure 5D:
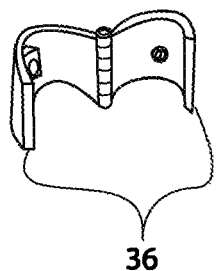
FIG. 5D is an expanded view of a portion of the attachment rings of an embodiment of the present invention.
Figure 6A:
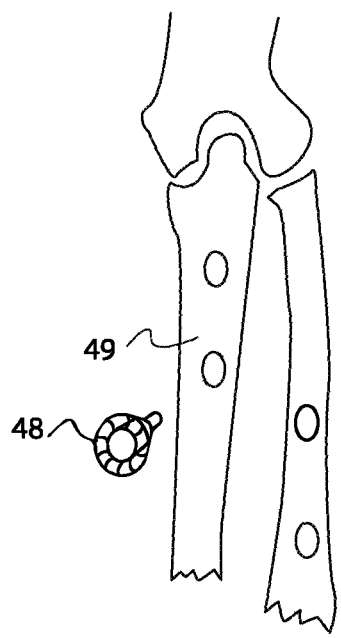
FIG. 6A is a side view of an embodiment of the present invention.
Figure 6B:
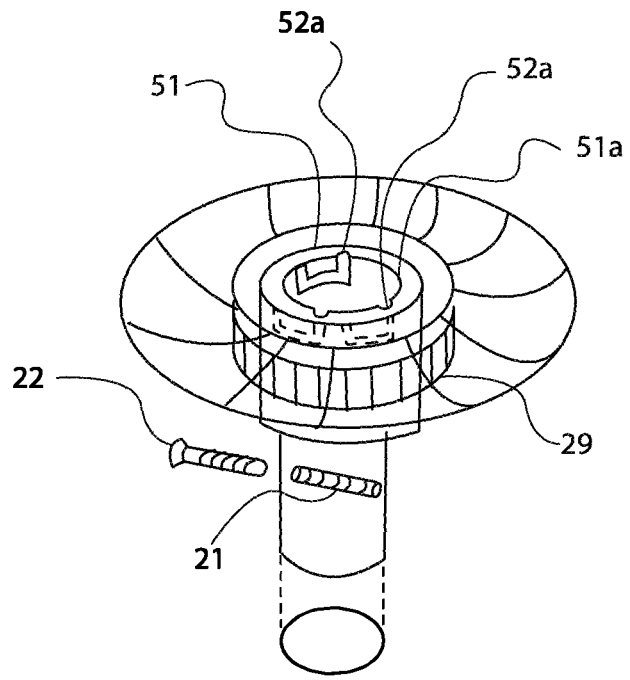
FIG. 6B is an expanded view of an embodiment of the present invention.
Figure 7:
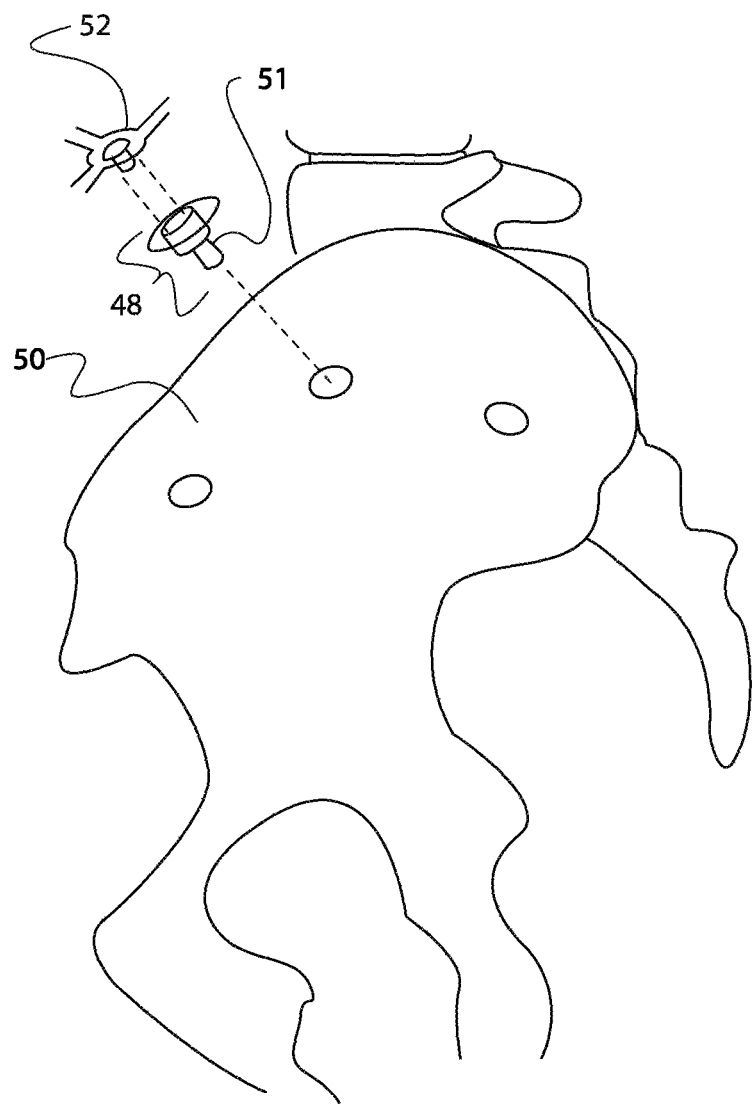
FIG. 7 is a top view of an embodiment of the present invention.
Figure 8A:
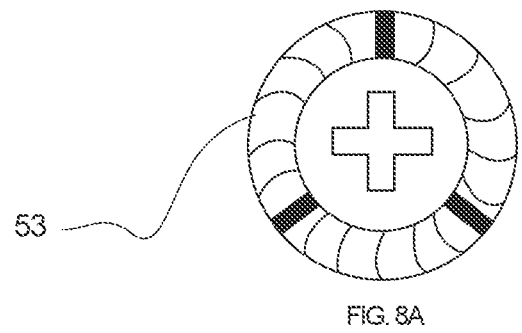
FIG. 8A is a top view of an embodiment of the present invention.
Figure 8B:
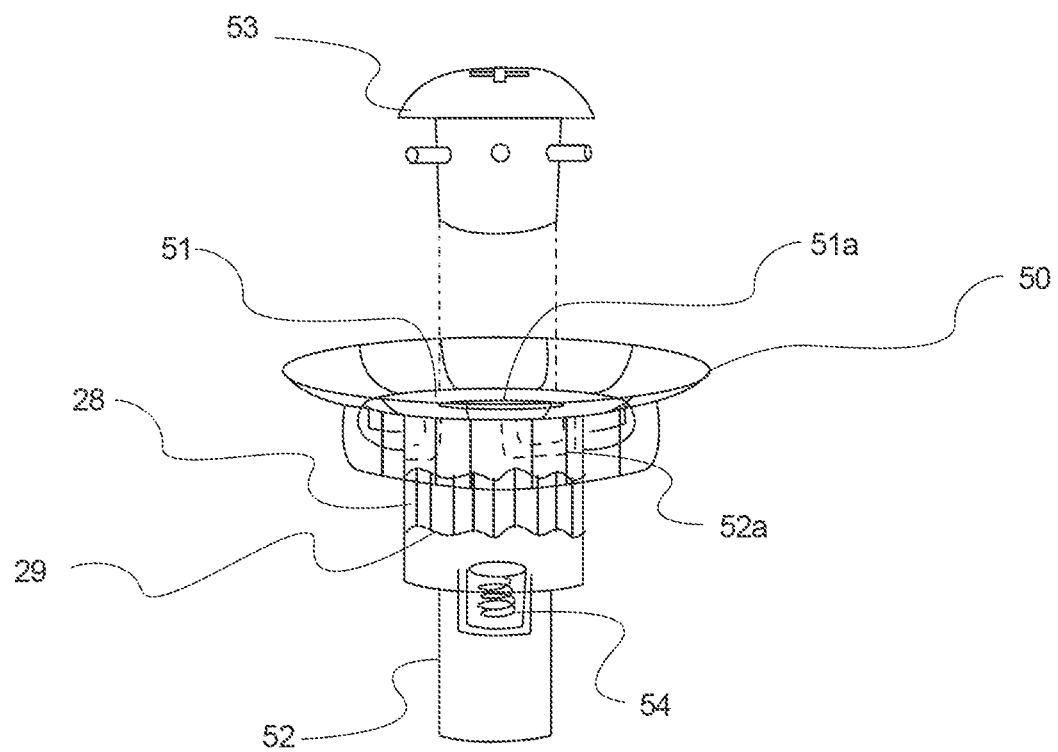
FIG. 8B is a side view of an embodiment of the present invention.
Figure 8C:
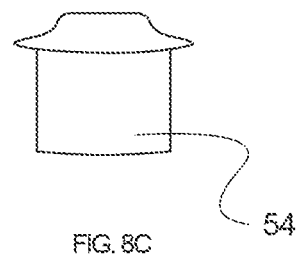
FIG. 8C is a side view of an embodiment of the present invention.

As best seen in FIGS. 4a-c, the PEEK-rings 30 and 31 attach to the transfer rod 19 at the slotted, gear-like interface area 29. The PEEK-rings that attach to muscle groups 30 has from one to four or more attachment flanges 40, designed as levers connecting between muscle/tendons and the I/O transfer rod 19. Muscle fibers 5 or tendons are surgically attached to the flanges 40 to provide intra-limb force transfer to the rod assemblies.

The PEEK-rings 31 have a metal, preferably nickel-titanium, mounting scaffold as a skeletal framework, with PEEK webbing-mesh 41 for suture and cyto-cellular attachment. The PEEK-rings for fascial and dermal attachment have a transitional web/mesh with the central area being solid PEEK with underlay of nickel-titanium scaffold. This transitions to a progressively "looser" web zone of PEEK and ends at the outer ring of metal scaffold, PEEK mesh and sub-mesh composed of collagen/allogenic hyaluronic acid (or other equivalent connective tissue biosynthetic substrate material) webbing.

It is into this PEEK/Collagen webbing which the fascia 6 or dermal 7 layers, as seen in FIG. 1 are sutured, and into which the fascia and derma will grow and interweave with for exclusion of any external environment when fully healed. Such interfaced healing may be augmented by the use of epidermal growth factors or vascular endothelial growth factors, or similar endovascular growth promoting bio-molecules.

Figure 9A:
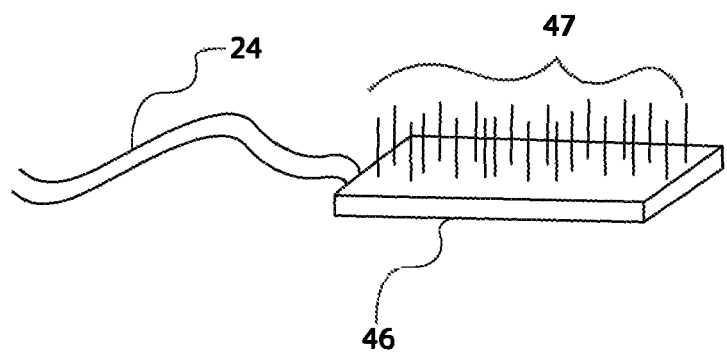
FIG. 9A is a side view of the Utah Array of an embodiment of the present invention.
Figure 9B:
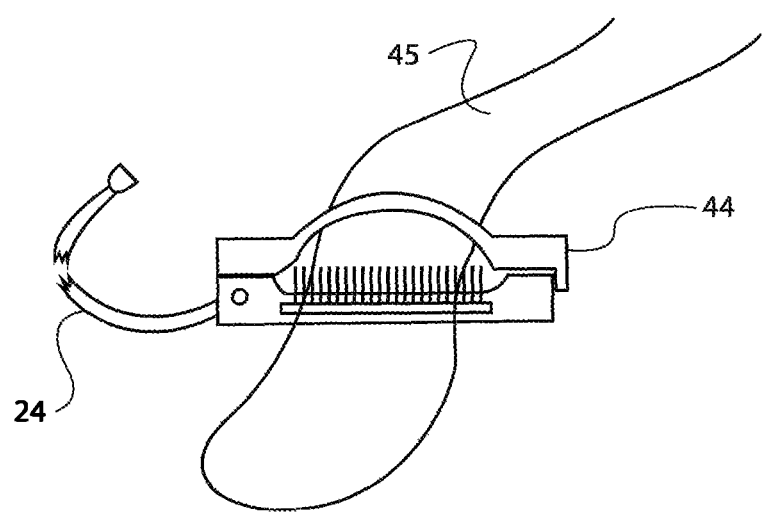
FIG. 9B is a side perspective view of a nerve clip of an embodiment of the present invention.

Referring to FIGS. 9A-9B, the micro-wire cables 24 attach to nerve/bundle clamps 44, that penetrate through each associated nerve sheath 45 into the nerve cytoplasm itself and clamp onto the nerve(s). The nerve(s) are penetrated by appropriately sized modified Utah Array (UA) carbon fiber spindles 47, which are integrated onto silicon on insulator (SOI) digital signal processor (DSP).

The SOI long dimension ranges from about 1 mm to about 5 mm, according to the size of the target nerve/bundle. The Utah Array is composed of about 100 nm diameter carbon fibers spaced about 100 nm apart, are about 5 mm to about 25 mm high, and are coated with sphingosine, or other nerve sheath cell related molecule. The carbon fiber coating allows for a more integrated transmembrane entry through the nerve sheath cell membrane and into the cellular cytoplasm.

Human nerves typically are 0.1-5 micrometers in diameter. Current generation integrated circuit transistor gate size is 14 nm. The DSP is configurable after implantation to group sets of the UA splines into functional groups and sensory or excitatory pathways.

The DSP detects the changes in the nerve cells' ion fluxes, surface potentials and internal voltages. It digitizes that information (24 bit) and serializes the information to allow connection 8 to exterior processing elements for transmission of the nerve signal data to the external environment. The nervous system connection and processing system also allows feedback signals to be returned to the nerve bundle by digital to analog processing via the same UA/DSP and potentials gated out to the UA array/nerve interface.

Referring to FIGS. 6A, 6B, 7, 8A, 8B and 8C, an additional type of prosthetic attachment 48 is shown mounted in transverse direction to a particular bone, such as the ulna (forearm) 49 or ileum (lateral pelvis) 50. These implants are meant for load bearing and external accessory attachment.

The central implant 51 has PEEK-ring zones for attachment to fascia and dermis, similar to areas 31, 40, and 41 in FIG. 4. The central mount 52 is metal, preferably nickel-titanium, and has a central channel 51a that is visible at the skin surface. A pronged-stud connector 53 fits into the channel 51a and provides mechanical connection to any mount via at least one pronged stud that inserts into locking channels 52a and turns into a locked position and is spring 54 pressure loaded into a held position.

Any attachment of appropriate size and purpose could mount to the accessory mount anchors, such as a load bearing backpack, additional attachments to a large manually operated tool, and so on.

A rubber plug 55 inserts into the empty stud central channel to keep the connector clean between uses.

Figure 10:
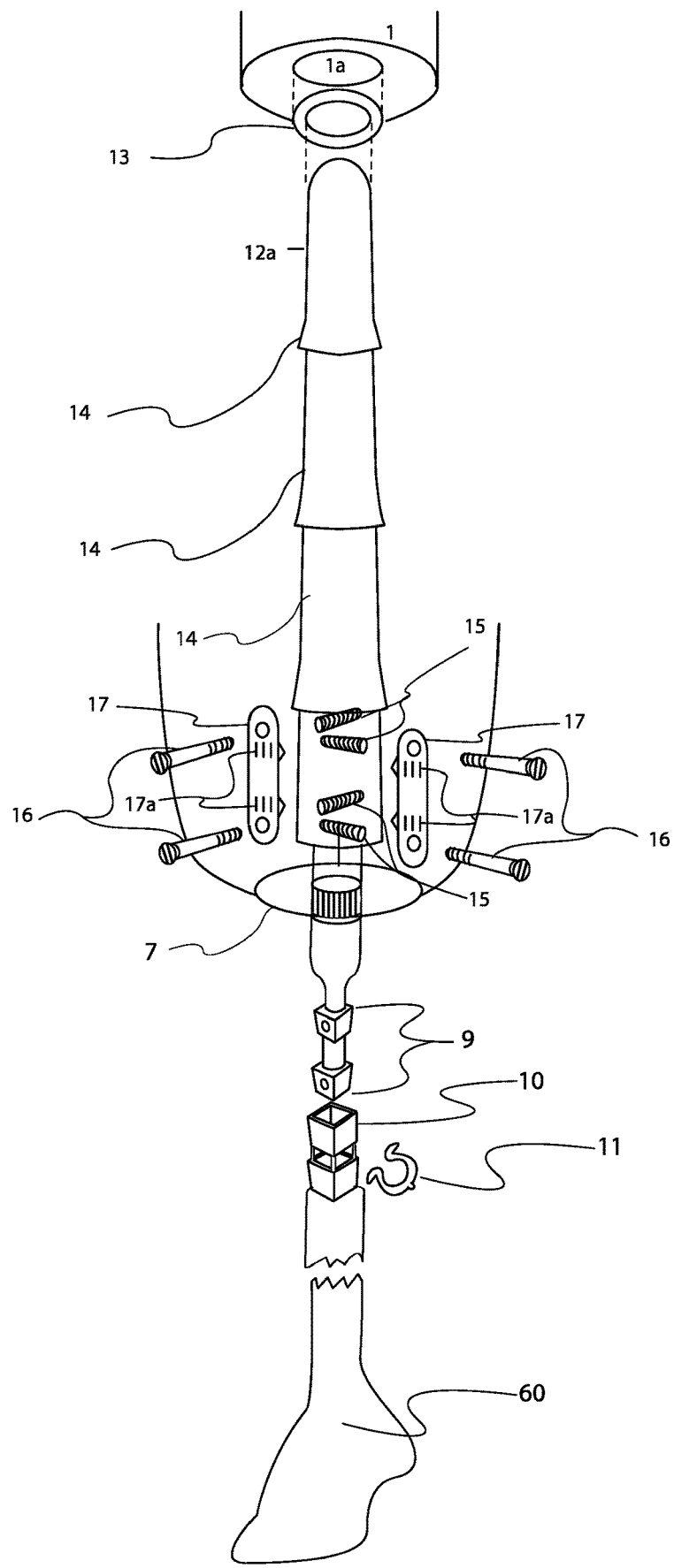
FIG. 10 is front view of an embodiment of the present invention.

Referencing FIG. 10, an embodiment is shown comprised generally of a long bone axial rod 12a configured to be inserted into the long bone 1 medullary cavity 1a which extends out from the long bone 1 to an exterior body attachment and includes attachment rings 7 for attaching muscle groups, fascia layers and dermal layers to the long bone axial rod 12a. The axial rod 12a exits the body and terminates in a male ratchet connector 9.

Further, a bottom portion 60 is shown, configured to connect with the long bone axial rod 12a utilizing female socket connectors 10 at one end into which the ratchet male connectors 9 are inserted using a ratchet retention spring ball system, not shown, and secured with a retention clip 11.

Further, the long bone rod 12a inserts into the long bone medullary cavity 1a. The rod is substantially oblong in cross section. The oblong cross section transfers rotational forces to the long bone 1 and keeps the implant from rotating within the long bone medullary cavity 1a.

The long bone rod 12a has wedge-like flare-anchors 14 along the length of the rod 12a. The implant flare-anchors 14 support the implant against extrinsic forces that will pull at the implant, such as carrying a weight in a prosthetic forearm. Additionally, the long-bone implant has mounting bores 15 through which screws 16 attach fixation plates 17 which are external to the rod 12a, and provide additional mounting stability against forces transmitting from the external environment to the long bone 1. As displayed in FIG. 10, a plurality of bore holes 15 and screws 16, may be utilized, and in embodiments fewer than shown may be used.

As best seen in FIG. 10, the fixation plates 17 have several rows of mounting teeth 17a to grip into the cortical bone as a structural interface. The long bone implant rod 12a is also the transfer rod to the external environment and allows the physical connection between the long bone rod 12a and the soft tissues of the limb utilizing attachment and/or polyetheretherketone (PEEK) rings 7, as best seen in FIG. 3. PEEK material can include semi-crystalline, high temperature plastics, and it can include any selection of bio-neutral polymers available, configured for surgical implantation purposes.

Although mechanical interfaces are illustrated, in embodiments not shown, hybrid versions can include a single axial rod and also allow for the neurologic connections described herein.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A system suitable for attachment of a device in a transverse direction to a bone comprising:
    a central bone implant with a substantially cylindrical hole extending therethrough and configured to embed into a bone;
    a subcutaneous central mount with a central channel extending therethrough and a plurality of locking channels along its interior perimeter;
    a substantially cylindrical stud connector with a plurality of prongs extending outwardly from exterior surface;
    a spring coil, wherein the central mount extends through the cylindrical hole of the central bone implant and is secured into place;
    wherein the stud connector locks into the central mount by inserting the prongs into the locking channels and turning clockwise into a locked position; and
    wherein the spring is coiled up and the central mount is pressure loaded into a locked position.

2. The system of claim 1 further comprising a rubber plug sized and dimensioned such that the plug secures into the cylindrical hole of the central bone implant when the stud connector is removed from the central mount and the rubber plug is inserted into the cylindrical hole in a press fit fashion.

3. The system of claim 1 further comprising connective tissue biosynthetic substrate material.

4. The system of claim 1 further comprising an attachment ring for attaching, at least one fascia layer and at least one dermal layer to the central bone implant.

5. The system of claim 4 wherein the attachment rings are constructed from a bio-neutral polymer suitable for surgical implantation of the body.

6. The system of claim 4 further comprising a transitional webbed area between the attachments rings and the fascia and dermal layers.

7. The system of claim 6 further comprising a metal mounting scaffold which forms a skeletal frame for the transitional webbed area.

8. The system of claim 7 wherein the webbed area has a central area closest to the attachment ring formed from the solid bio-neutral polymer on the skeletal frame and as the webbing extends to the fascia and dermal layer the webbing is formed from progressively less bio-neutral polymer and progressively more of the connective tissue biosynthetic substrate material.

9. The system of claim 6 wherein the fascia and dermal layer interweave with the webbed area.

10. The system of claim 9 further comprising endovascular growth promoting bio-molecules wherein the endovascular growth promoting bio-molecules promote the fascia and dermal layer interweaving with the webbed area.

* * * * *